United States Patent [19]

Ziman

[11] 4,311,849

[45] Jan. 19, 1982

[54] PROCESS FOR MAKING 3-(N-ARYLAMINO)-GAMMA-BUTYROTHIOLACTONES

[75] Inventor: Stephen D. Ziman, San Francisco, Calif.

[73] Assignee: Chevron Research, San Francisco, Calif.

[21] Appl. No.: 184,846

[22] Filed: Sep. 8, 1980

[51] Int. Cl.$^3$ .......................................... C07D 333/24
[52] U.S. Cl. .................................................. 549/63
[58] Field of Search ......................................... 549/63

[56] References Cited

FOREIGN PATENT DOCUMENTS 611437 12/1960 Canada .................................. 549/63
1081466 10/1960 Fed. Rep. of Germany ........ 549/63

*Primary Examiner*—Alan Siegel
*Attorney, Agent, or Firm*—J. A. Buchanan, Jr.; T. G. DeJonghe; L. S. Squires

[57] ABSTRACT

A novel process for making 3-(N-arylamino)-gamma-butyrothiolactones from their corresponding butyrolactone analogs is disclosed. The thiolactone products are useful intermediates for making fungicidal compounds.

9 Claims, No Drawings

PROCESS FOR MAKING 3-(N-ARYLAMINO)-GAMMA-BUTYROTHIOLACTONES

BACKGROUND OF THE INVENTION

In commonly assigned Belgian Pat. No. 871,668 are disclosed fungicidal 3-(N-acyl-N-arylamino)-gamma-butyrothiolactones. Such compounds are made in two steps by the alkylation and acylation of an arylamine.

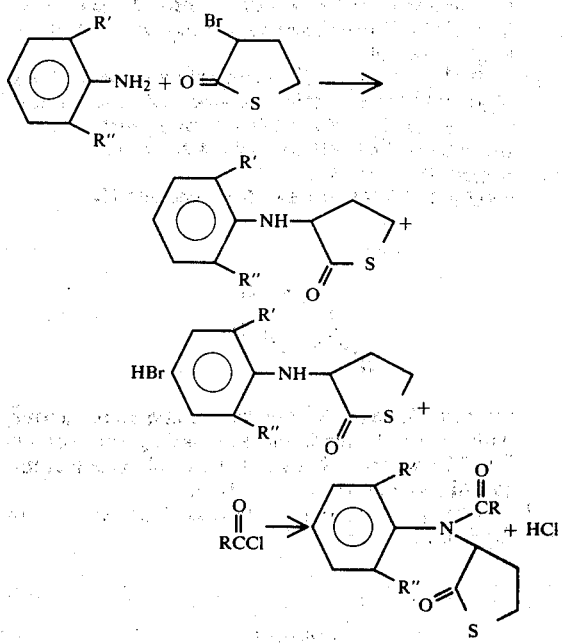

In *J. Org. Chem.*, 28, pp. 964–7 (1963), Truce et al. disclose the internal cleavage of alkylmercapto-butyryl chlorides to butyrothiolactone, alkyl chlorides and alkenes by vacuum distillation.

SUMMARY OF THE INVENTION

I have found that 3-(N-arylamino)-gamma-butyrothiolactone intermediates, such as those disclosed in the above Belgian patent, may be made directly from the corresponding 3-(N-arylamino)-gamma-butyrolactones by reaction with a salt of an alkyl mercaptan, followed by treatment with a reagent conventionally used for converting carboxylic acid to its corresponding acid halide.

The 3-(N-arylamino)-gamma-butyrolactones, which may be used as starting materials in the practice of my invention, are disclosed in the above Belgian patent, as well as in commonly assigned U.S. Pat. Nos. 3,933,860 and 4,107,323, copending applications Ser. No. 13,856, filed Feb. 22, 1979, and Ser. No. 44,740, filed June 1, 1979, the disclosures of which are incorporated herein by reference. Other butyrolactone starting materials are disclosed in Belgian Pat. No. 863,615.

Other 3-(N-arylamino)-gamma-butyrolactone starting materials are disclosed in commonly assigned U.S. Ser. No. 68,243, filed Aug. 17, 1979, the disclosure of which is incorporated herein by reference.

The 3-(N-arylamino)-gamma-butyrothiolactones produced in accordance with my invention are useful intermediates for making fungicidal 3-(N-acyl-N-arcylamino)-gamma-butyrothiolactones. Such fungicidal compounds are disclosed in Belgian Pat. No. 871,668, and in U.S. application Ser. No. 13,856, filed Feb. 22, 1979 and Ser. No. 44,740, filed June 1, 1979.

DESCRIPTION OF THE INVENTION

According to my invention, a butyrolactone compound of the following Formula II is used as a starting material:

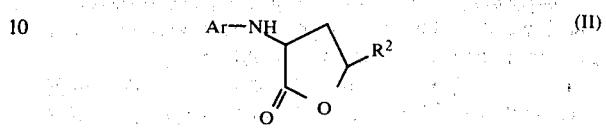

wherein

Ar is phenyl, naphthyl, phenyl or naphthyl substituted with 1 to 4 of the same or different substituents selected from fluoro, chloro, bromo, iodo, alkyl of 1 to 4 carbon atoms, alkoxy of 1 to 4 carbon atoms or nitro;

$R^2$ is hydrogen, alkyl of 1 to 6 carbon atoms, phenyl or phenyl substituted with 1 to 2 of the same or different substituents selected from fluoro, chloro, bromo and alkyl of 1 to 6 carbon atoms.

The compound of the formula II is first treated with the salt, preferably the sodium salt, of an alkyl mercaptan, RSNa, wherein R contains from 1 to 10 carbon atoms. Although the sodium salt of the alkyl mercaptan is preferred, other monovalent carbon salts may be used, such as the potassium, lithium or ammonium salt, i.e., $RS^-M^+$, wherein $M^+$ is a monovalent cation and R is as defined above. The acid product of this first reaction is then treated with a reagent, such as phosphorus trichloride, which is capable of converting a carboxylic acid to its corresponding acid halide. While not intending to restrict my invention to any particular reaction mechanism, the process of my invention may be depicted as follows:

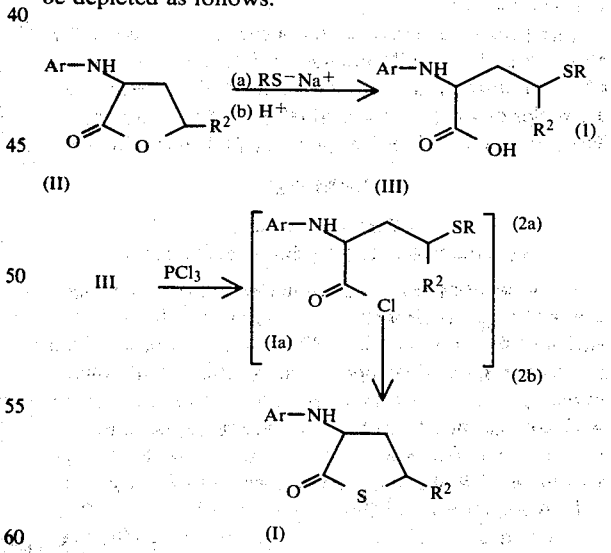

Reaction (1) may be performed in a suitable inert solvent at from about 0° C.–100° C., preferably in the range of 40° C.–80° C. Substantially equimolar portions of the butyrolactone (II) and salt of the alkyl mercaptan (RSNa) are used. Suitable solvents include dimethoxyethane, chlorinated hydrocarbons, dioxane, and tetrahydrofuran. The reaction pressure is not critical and may be conveniently selected. Generally, atmospheric pressure is used. The reaction is generally complete within one to four hours. The product acid (III) may be isolated by conventional procedures such as extraction, filtration, chromatography, etc. The nature of the alkyl mercaptide, RSNa, is particularly critical for obtaining the highest yield of desired product. Tertiary alkyl mercaptides are preferable to secondary and primary alkyl mercaptides. Secondary alkyl mercaptides are preferable to primary alkyl mercaptides.

Reaction (2a) is shown above as performed with phosphorus trichloride, however, any reagent known to convert carboxylic acids to acid halides may be used. Examples of such reagents are thionyl chloride, phosphorus pentachloride and oxalyl chloride.

Reaction (2a) may be conducted in an inert solvent from about 0° C.-30° C. An excess of the stoichiometric amount of $PCl_3$ is normally used.

After addition of $PCl_3$, the mixture is stirred to effect the cleavage reaction (2b). This reaction may be conducted from ambient temperature to about 100° C. The thiolactone procuct (I) is separated from the reaction mixture by conventional methods, i.e., extraction, filtration, chromatography, crystallization, etc.

Particularly preferred solvents for my process are dialkyl glycols, preferably dimethoxyethane, and chlorinated hydrocarbons, preferably methylene chloride. On large-scale runs, a solvent would not be necessary since sufficient $PCl_3$ would be present to serve as a reaction medium. Reactions (2a) and (2b) may be carried out at any convenient pressure, preferably atmospheric pressure.

While use of a solvent may be used in the practice of reactions (2a) and (2b), the $PCl_3$ may be added directly to the acid (III), if the acid is a liquid. The thiolactone product (I) may then be isolated by conventional purification procedures.

The preferred molar ratio for reaction (1) is 1:1 for the starting lactone (I) and mercaptide salt. For reaction (2a), if phosphorus trichloride is used, the stoichiometric molar ratio of 3:1 for acid (III) to $PCl_3$ may be used. However, a 6 to 7 molar excess of $PCl_3$ is preferred.

EXAMPLE

Preparation of
3-(2,6-dimethylanilino)-butyrothiolactone

A. A solution of 3-(2,6-dimethylanilino)-butyrolactone (11.89 g.) in dimethoxy ethane was added to 6.5 g. sodium t-butylmercaptide. The solution was refluxed for four hours and stripped. The residue was dissolved in water, acidified with hydrochloric acid and extracted with methylene chloride. The organic phase was collected, dried ($MgSO_4$) and stripped to yield 15.2 g. viscous oil (IR spectrum shows presence of —$CO_2H$).

B. A 5 g. portion of the oil was stirred in 10 ml. (15.7 g.) phosphorus trichloride at room temperature for two days. The excess phosphorus trichloride was stripped at 60° C. and the residue was dissolved in methylene chloride, washed with water and dried. The residue was purified on a silica gel column to yield 1.31 g. of product (Yield 34.8%).

What is claimed is:
1. A process for the preparation of a compound of the Formula (I):

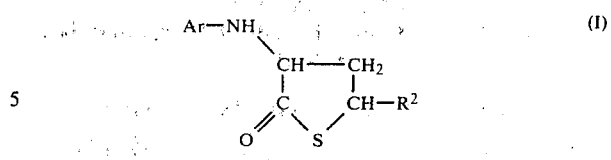

wherein
Ar is phenyl, naphthyl, phenyl or naphthyl substituted with 1 to 4 of the same or different substituents selected from fluoro, chloro, bromo, iodo, alkyl of 1 to 4 carbon atoms, alkoxy of 1 to 4 carbon atoms or nitro;
$R^2$ is hydrogen, alkyl of 1 to 6 carbon atoms, phenyl or phenyl substituted with 1 to 2 of the same or different substituents selected from fluoro, chloro, bromo and alkyl of 1 to 6 carbon atoms;
comprising the steps of:
(a) reacting a compound of the Formula (II):

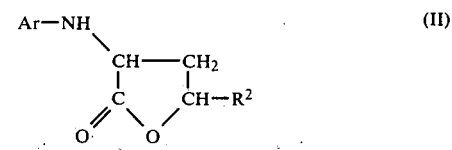

wherein Ar and $R^2$ are as defined hereinabove; with an alkyl mercaptan salt having the formula $RS^-M^+$ wherein R is alkyl of 1 to 10 carbon atoms and $M^+$ is a monovalent cation;
(b) reacting a compound produced from step (a) of the Formula (III):

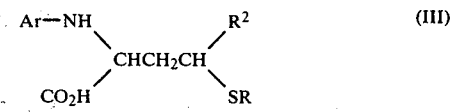

wherein Ar, R and $R^2$ are as defined hereinabove with a reagnet capable of converting a carboxylic acid to the corresponding acid halide to form a compound of the formula (I).

2. The process of claim 1 wherein R is tertiary butyl, $M^+$ is $Na^+$ and the reaction employed in step (b) is phosphorus trichloride.

3. The process of claim 2 wherein Ar is 2,6-dialkylphenyl and $R^2$ is hydrogen.

4. The process of claim 3 wherein Ar is 2,6-dimethylphenyl.

5. The process of claim 1 wherein said step (a) is conducted at temperatures in the range of about from 0°-100° C. using substantially equimolar portions of the compound of Formula (II) and said alkyl mercaptan salt.

6. The process of claim 1 wherein said reagent of said step (b) is phosphorus trichloride.

7. The process of claim 6 wherein said step (b) is initially conducted at temperatures in the range of about from 0° to 30° C. to effect cleavage of the lactone moiety of the product of said step (a) and then conducted at temperatures in the range of about from ambient temperature to 100° C.

8. The process of claim 5 wherein said reagent of step (b) is phosphorus trichloride.

9. The process of claim 8 wherein said step (b) is initially conducted at temperatures in the range of about from 0° to 30° C. to effect cleavage of the lactone moiety of the product of said step (a) and then conducted at temperatures in the range of about from ambient temperature to 100° C.

* * * * *

UNITED STATES PATENT AND TRADEMARK OFFICE
CERTIFICATE OF CORRECTION

PATENT NO. : 4,311,849

DATED : January 19, 1982

INVENTOR(S) : STEPHEN D. ZIMAN

It is certified that error appears in the above-identified patent and that said Letters Patent are hereby corrected as shown below:

Col. 2, line 30 "carbon" should read --cation--.

Col. 4, line 43 "reaction" should read --reagent--.

Signed and Sealed this

Twentieth Day of April 1982

[SEAL]

Attest:

GERALD J. MOSSINGHOFF

Attesting Officer

Commissioner of Patents and Trademarks